United States Patent [19]

Leiberich

[11] 4,373,699
[45] Feb. 15, 1983

[54] FLUID FLOW CONTROL VALVE FOR DENTAL INSTRUMENTS

[75] Inventor: Hermann Leiberich, Karlsruhe, Fed. Rep. of Germany

[73] Assignee: Sybron Corporation, Rochester, N.Y.

[21] Appl. No.: 149,909

[22] Filed: May 15, 1980

[51] Int. Cl.³ .............................................. F16K 31/06
[52] U.S. Cl. .................................... 251/139; 251/141
[58] Field of Search ............................... 251/139, 141

[56] References Cited

U.S. PATENT DOCUMENTS

| 3,125,321 | 3/1964 | Domclew | 251/139 |
| 3,285,285 | 11/1966 | Bielefeld | 251/139 X |
| 3,820,757 | 6/1974 | Siebel | 251/139 |
| 4,002,202 | 1/1977 | Huebsch | 251/139 X |

Primary Examiner—Arnold Rosenthal
Attorney, Agent, or Firm—Theodore B. Roessel; Roger Aceto

[57] ABSTRACT

A fluid flow control valve uses a solenoid to control flow wherein the fluid path extends axially through the core of the solenoid. Flow is variable over the range of 0 to maximum flow and varies linearly with the voltage applied to the solenoid coil.

4 Claims, 2 Drawing Figures

U.S. Patent   Feb. 15, 1983   4,373,699
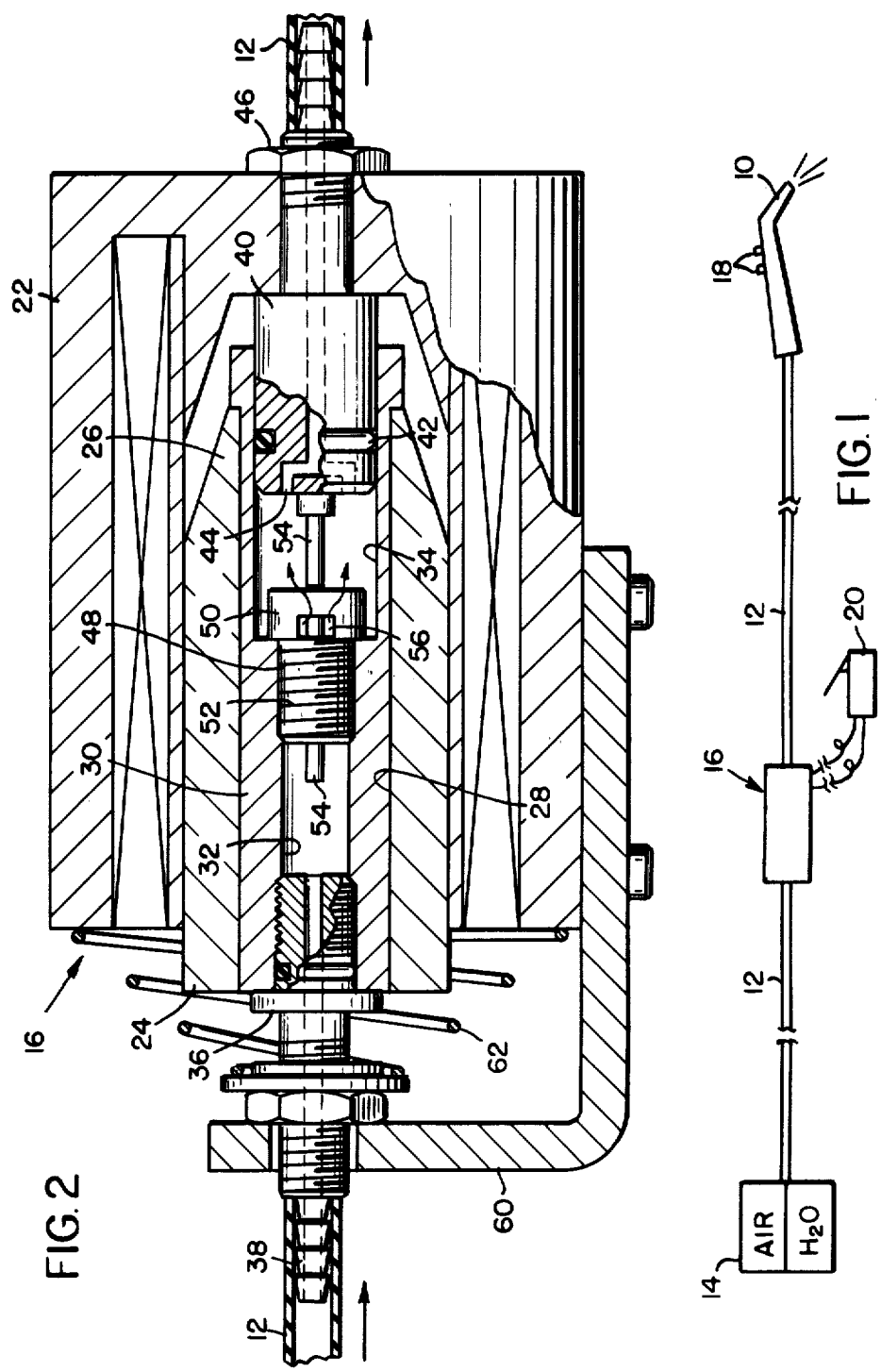

FLUID FLOW CONTROL VALVE FOR DENTAL INSTRUMENTS

BACKGROUND OF THE INVENTION

The present invention relates generally to fluid flow control valves for dental instruments and more particularly to a solenoid operated control valve wherein fluid flow is directly proportional to the voltage applied to the solenoid coil.

Control valves are widely used in dental instrumentation to control flow of fluids such as air and water to various instrumentation such as syringes and dental hand pieces. In the case of a syringe, for spraying water, air or a combination of water and air, fluid flow is usually controlled by mechanical valve located within the body of the syringe and operated by depressing a suitable lever or pushbutton on the syringe which is mechanically attached to the valve mechanism (see, for example, U.S. Pat. No. 3,988,001). It is also known to have such a mechanically operated valve incorporated into a foot switch so that flow of fluid from the syringe can be controlled at some point remote from the syringe.

Solenoid operated flow valves are also known in the dental art, but it is believed that in such cases the solenoid is merely to put a valve in the full open or full closed position. Although proportional solenoids are known, it is not believed that they heretofore have been utilized in the dental field to control the flow of fluid to syringes as in the present invention nor have such valves been constructed as the valve of the present invention.

SUMMARY OF THE INVENTION

The present invention may be characterized in one aspect thereof as means for controlling fluid flow including a solenoid of the type wherein the magnetic force applied to the solenoid core varies linearly with the voltage applied to the solenoid coil. The core of the solenoid has an axial passage therethrough, one end of the passage being adapted for connection to a source of fluid under pressure and the other end of the passage being an exit for the fluid flowing through the core. Within the axial passage is a valve member having a valve body fixed to the core and a valve stem. The stem is arranged so that movement of the core responsive to voltage applied to the solenoid coil opens the valve permitting flow of fluid through the axial passage in the core. Means extending into the exit end of the axial passage creates a back pressure responsive to the flow of fluid which tends to offset in part the magnetic force induced in the core. This offsetting force maintains the valve in a partly open position. As more voltage is applied to the coil, the linear movement of the core increases to further open the valve. In turn, the increased fluid flow increases the back pressure to keep the valve from fully opening. In this fashion, flow of fluid through the solenoid is controlled over the full range from 0 to maximum flow.

DESCRIPTION OF THE DRAWINGS

FIG. 1 is a schematic view showing a dental syringe employing the present invention; and FIG. 2 is a view partly broken away and in section showing the fluid flow controlling solenoid of the present invention.

DESCRIPTION OF THE PREFERRED EMBODIMENTS

Referring to the drawings, FIG. 1 shows a dental instrument 10, such as a syringe or the like. The dental syringe is connected by suitable tubing 12 to a source of air and water 14. Between the utility source 14 and the instrument 12 is one or more solenoid valves of the present invention generally indicated at 16. Operation of solenoid valve 16 can be accomplished either by manipulation of push buttons 18 on the syringe (one for air and other for water) or by operation by some remote switch 20 such as a foot switch. It should be appreciated at one solenoid valve 16 is provided for controlling each utility, but that the operation of either foot switch 20 or push buttons 18 would control both air and water flow depending upon which utility source was previously selected.

Referring to FIG. 2, the solenoid fluid control valve 16 of the present invention includes a conventional solenoid coil 22. Within solenoid coil 22 is a solenoid core 24 which is drawn into the coil when the coil is energized.

As shown in FIG. 2, end 26 of the core is tapered. This taper modifies the magnetic characteristics of the core so that the magnetic force applied to the core for drawing the core into the coil varies linearly with the voltage applied to the solenoid coil 22 over a wide range of pull of the core.

Core 24 has an axial bore 28 into which a sleeve 30 is inserted by press fitting or other suitable means. Extending through the sleeve from one end to the other is an axial passage. One section 32 of this passage has a diameter which is smaller than a second section 34 of this passage. The smaller section 32 is the inlet side of the solenoid core whereas the section 34 of larger diameter is the outlet side of the core. Threaded to the inlet section 32 of the solenoid core is any suitable coupling member 36. This coupling member has a nipple 38 for attachment to the flexible tubing 12 which connects the solenoid to the utility source 14 (FIG. 1).

Fixed to solenoid coil 22 and slidably extending into the outlet section 34 of the solenoid core is a plug 40. An O-ring seal 42 about the plug renders this sliding engagement fluid tight. To permit flow of fluid from the outlet section 34, the plug 40 is provided with appropriate channels 44. These channels extend through the plug and communicate with a coupling 46 which in turn connects the fluid line 12 to the dental syringe 10. The cross sectional area of channels 44 is considerably less than the cross sectional area of outlet section 34 for purposes set out hereinbelow.

Within sleeve 30 between the two sections 32, 34 of the core passage is a valve 48. Valve 48 is conventional in construction having a body 50 which is fixed to sleeve 30 by any suitable means such as by threads 52 as shown in FIG. 2. Valve 48 is normally closed so that it seals the inlet section 32 of the core from the outlet section 34. Extending through valve body 50 is a valve stem 54 which has one end butted against plug 40. The axial movement of this stem opens or closes valve ports 56. In particular, it should be appreciated that movement of valve stem 54 with respect to the valve body 50 and to the left as viewed in FIG. 2 opens valve ports 56. This allows fluid to flow from the inlet section 32 through valve 48 and out of ports 56 into the outlet section 34 of the axial passage.

Completing the structure of the solenoid valve 16 is an L-shaped bracket 60 and a coil spring 62. The disposition and operation of coil spring 62 is such that it urges solenoid coil 24 outward from solenoid coil 22 and against bracket 60. With this arrangement valve 48 within the solenoid core is normally closed absent the application of a voltage to coil 22.

The operation of the present invention will be described beginning with the valve in the condition as shown in FIG. 2, namely, a closed position. When fluid flow is desired, either push buttons 18 or the foot switch 20 can be operated. This applies a voltage to solenoid coil 22 for energizing the coil. As set out hereinabove, core 24 is designed so that the magnetic forces acting on the core to draw it into the solenoid coil are directly and linearly proportional to the voltage applied to the coil over a wide range of the pull of the core. Thus, the greater the voltage applied to the coil, the greater will be the forces acting on the core tending to move it into the coil or to the right as viewed in FIG. 2.

Assume first a low voltage is supplied just sufficient to overcome the bias of spring 62, so that core 24 does move to the right as viewed in FIG. 2. Since one end of valve stem 54 is butted against piston 40, such movement of the core will move valve body 50 to the right with respect to valve stem 54 and the valve will open. The opening of the valve allows fluid under pressure to flow from the inlet section 32 of the axial passage and into the outlet section 34. Fluid in the outlet section 34 then passes through channels 44 in plug 40 and out of the solenoid to the syringe 10.

The cross sectional area of the outlet section 34 is very much larger than the cross sectional area of channels 44. This produces a resistance to flow of the fluid through piston 40 and causes a pressure rise within outlet section 34. This increase in pressure in the outlet section tends to move solenoid core 24 to the left as shown in FIG. 2.

As soon as the core begins to move to the left, valve 48 begins to close. This decreases flow and in turn the pressure in outlet section 34 begins to drop. Even a small drop in the pressure in outlet section 34 allows the applied magnetic force to begin pulling the core back into the solenoid against the bias of spring 62 thereby increasing the vlave opening. In this manner, a high frequency flutter is established which maintains valve 48 in a partly open position directly proportional to the voltage applied to solenoid coil 22.

If maximum fluid flow is desired, foot switch 20 or push buttons 18 are fully depressed applying the maximum voltage to solenoid coil 22 so that the force tending to pull core 24 into the coil completely overcomes the resistance to this motion offered by spring 62 and the net pressure in outlet section 34. When the voltage applied to the coil 22 is removed, the operation of spring 62 moves core 24 back to the position as shown in FIG. 2, to close the valve.

Thus, the present invention adapts a proporational solenoid for use as a fluid flow control valve wherein the flow of fluid is through the solenoid core, such flow being controlled over the entire range of flow from zero to maximum flow. Such control is accomplished simply by varying the voltage applied to the solenoid valve. Further, the valve of the present invention makes it possible to control the flow of fluid from either the dental instrument itself, such as from push buttons 18 or by use of some remote switch such as a foot peddle 20.

Having thus described the invention in detail, what is claimed as new is:

1. A fluid flow control valve for varying the flow of fluid in a range from zero to maximum flow directly responsive to an applied voltage said valve comprising:
   (a) a solenoid including a coil and a core;
   (b) said core having a fluid passage extending axially therethrough, the inlet of said passage being adapted for connection to a source of fluid under pressure and the outlet of said passage being an exit for fluid flowing through said core;
   (c) valve means fixed to said core within said axial passage for movement with said core, said valve means being located between said inlet and outlet wherein the movement of said core responsive to a voltage applied to said coil opens said valve means and permits fluid flow through said axial passage; and
   (d) means in said axial passage down stream from said valve mans for creating fluid pressure in said axial passage responsive to the flow of fluid therethrough, said fluid pressure acting on said core in a direction for offsetting the magnetic force induced in said core by the voltage applied to said coil.

2. A fluid flow control valve as in claim 1 including a plug extending into said outlet portion, said plug being in sliding fluid tight engagement with said outlet portion, said plug having a channel therethrough providing the sole passage for fluid from said outlet portion and being of a size for producing a resistance to flow of fluid through said plug.

3. A fluid flow control valve as in claim 2 wherein said valve means has a valve body fixed to said core and a valve stem butted against said plug, said stem being movable with respect to said valve body whereby movement of said core opens said valve means.

4. A fluid flow control valve for dental syringes or the like comprising:
   (a) a solenoid including a coil and a core, said core being tapered such that the magnetic force attracting the core into the solenoid varies linearly with the voltage applied to the coil;
   (b) said core having an axial inlet passage for connection to a source of fluid under pressure and an axial outlet passage;
   (c) a valve fixed in said core intermediate said inlet and outlet passages;
   (d) a plug fixed to said coil and extending slidably into said core outlet passage, said plug having a channel therethrough arranged to provide an exit for fluid from said outlet passage which produces a resistance to the flow of fluid through said plug; and
   (e) a valve actuator extending between said plug and said valve for opening said valve responsive to movement of said core towards said plug.

* * * * *